(12) United States Patent
Tseng et al.

(10) Patent No.: US 9,023,613 B2
(45) Date of Patent: May 5, 2015

(54) SPERM SELECTING SYSTEM AND THE METHOD THEREOF

(71) Applicant: National Tsing Hua University, Hsinchu (TW)

(72) Inventors: Fan-Gang Tseng, Hsinchu (TW); Jen-Kuei Wu, Hsinchu (TW); Peng-Chun Chen, Hsinchu (TW)

(*) Notice: Subject to any disclaimer, the term of this patent is extended or adjusted under 35 U.S.C. 154(b) by 0 days.

(21) Appl. No.: 13/760,923

(22) Filed: Feb. 6, 2013

(65) Prior Publication Data

US 2014/0051112 A1    Feb. 20, 2014

(51) Int. Cl.
| | |
|---|---|
| *C12N 5/076* | (2010.01) |
| *C12M 1/34* | (2006.01) |
| *C12M 3/00* | (2006.01) |
| *C12N 5/071* | (2010.01) |
| *B01L 3/00* | (2006.01) |

(52) U.S. Cl.
CPC .............. *C12N 5/0612* (2013.01); *C12M 3/00* (2013.01); *B01L 3/502* (2013.01)

(58) Field of Classification Search
CPC .......... C12N 5/0612; C12N 5/061; A01N 1/02
USPC ........................ 435/287.1, 286.5, 2
See application file for complete search history.

(56) References Cited

U.S. PATENT DOCUMENTS 5,296,375 A * 3/1994 Kricka et al. ..................... 435/2

OTHER PUBLICATIONS

Koyama et al., Chemotaxis Assays of Mouse Sperm on Microfluidic Devices, Anal. Chem. 2006, 78, 3354-3359.*
Chemotaxis assays of mouse sperm on microfluidic devices—Anal Chem May 2006.

* cited by examiner

*Primary Examiner* — Jon P Weber
*Assistant Examiner* — Kara Johnson
(74) *Attorney, Agent, or Firm* — Richard C. Vershave; Foster Pepper PLLC

(57) ABSTRACT

The present invention discloses a sperm selecting system and the method thereof. The brief concept of the present invention is to generate a flow field by hydraulic pressure difference then utilize the property that the sperm swims against the flow field so as to difference the sperms by vitality thereof. One of the main features of the present invention is that the sperms be selected are initially set at the entrance of the flow field instead of the exit of the system. Furthermore, an activating design can be selectively added to the present invention so as to activate the sperm be affected by the process of freeze storing.

4 Claims, 4 Drawing Sheets

SPERM SELECTING SYSTEM AND THE METHOD THEREOF

PRIORITY CLAIM

This application claims the benefit of the filing date of Taiwan Patent Application No. 101128933, filed Aug. 10, 2012, entitled "A SPERM SELECTING SYSTEM AND THE METHOD THEREOF," and the contents of which is hereby incorporated by reference in its entirety.

FIELD OF THE INVENTION

The present invention relates to a sperm selecting system and the method thereof. More particularly, the present invention relates to sperm selecting system and the method thereof which utilize the property that the sperm swims against the flow field so as to difference the sperms by vitality thereof.

BACKGROUND OF THE INVENTION

According to the statistics by the World Health Organization, there are about 15% couples have infertility problems. Additionally, the half of infertility problems is due to the males so that the quality and the vitality of the sperms are important. Currently, the method of artificial insemination technology can be divided into three methods according to the quality and the vitality of the sperms. The first method is the artificial insemination which was developed for the infertility patients. The method is to inject the sperms into the uterus for fertilizing the ovum. The method is used when the sperm numbers of the patients are less than twenty millions per milliliter. It spends about 20 to 22 hours if the active sperms are more than two thousands. The second method is in vitro fertilization (IVF), generally known as the "test tube baby". The method is to let the fertilized egg be fertilized in vitro fertilization and then implant the embryo back to the uterus. The method is used when the sperm numbers of the patients are less than ten millions per milliliter. It spends about 20 to 22 hours if the active sperms are at least two thousands to ten thousands. The third method is intracytoplasmic sperm injection (ICSI). The method is to inject a sperm into the ovum by a microcatheter. The method is used when the sperm numbers of the patients are less than ten millions per milliliter. It spends about 14 to 16 hours with only a few active sperms. In prior art, the assisted reproductive program needs a lot of sperms and costs long time. Accordingly, it is important to develop a method to select the better sperms.

In prior art, the activities of the sperms would be estimated by a microscope. However, the sperms could not be selected. Accordingly, a sperms selecting systems were developed by the counter-flowed feature of the sperms. Specifically, the sperms are set at an exit of a channel and a fluid will be input from an entrance, so that the sperms will swim from the entrance toward the exit. Thus, the active sperms will reach the entrance for selecting the sperms. The public patent 201109654 of ROC can be refereed.

Please refer to another reference "A. B. S. Cho al in 2nd Annual International IEEE-EMBS ecial Topic conference on Microtechnologies in Medicine & Biolog, pp 156-159, 2002". The reference discloses that to select the sperms by a steady flow. The steady flow is created by the height difference and the net hydraulic pressure. Thus, the active sperms will reach the collecting groove of the extremity 131C. However, the sperms will be dead after burning out and the attrition rate of the sperms cannot be reduced. Additionally, the sperms also cannot be selected effectively.

In prior art, freeze storing is a common method. Thus, not all of the sperms will recover after thawing. Accordingly, the sperms cannot be selected easily to remove the weak sperms directly in prior art.

Accordingly, how to develop a sperm selecting system to reduce the attrition rate of the sperms and let the user obtain the selected sperms is an important issue in the prior art.

SUMMARY OF THE INVENTION

Accordingly, a scope of the invention is to provide a sperm selecting system for selecting a plurality of active sperms from an analyte. The sperm selecting system comprises a fluid supply module, a fluid collection module and a flow channel module. The flow channel module comprises an entrance, a working section and an exit. The entrance is connected to the fluid supply module. The exit is connected to the fluid collection module. The working section is disposed between and connected to the entrance and the exit. The working section comprises an initial section disposed on the flow channel module corresponding to the entrance.

In practice, the analyte is set in the initial section. The fluid supply module inputs a fluid with a specified flow rate to the fluid collection module. The plurality of active sperms can swim against the flow and stay in place. The plurality of sperms without activities will be flowed to the fluid collection module.

In practice, the flow channel module comprises a diverging section and the diverging section enlarges toward the exit. Additionally, the flow channel module comprises an activation section. The flow rate of the fluid in the activation section is at least three times faster than the specified flow rate. Furthermore, the activation section comprises an activation structure. The activation structure is disposed in the flow channel module for decreasing the flowing area of the perpendicular tangent plane for the fluid. Wherein, the activation structure is a dumbbell shaped activation structure and comprises a head end, a connecting end and an extremity. The connecting end is disposed between the head end and the extremity. The head end, the connecting end and the extremity are perpendicular to the flowing direction of the fluid for letting the fluid flow backward through the two ends of the activation structure.

Additionally, the head end, the connecting end and the extremity are surrounded by a sperm-collecting groove for storing the sperm. The sperm-collecting groove comprises a depth. The groove's direction of the depth and the flowing direction of the fluid are the same.

The flow channel module can comprises an activation section and an adhesive section. The adhesive section is adjacent and connected between the activation section and the initial section. The average area of the perpendicular tangent plane of the flow channel module in the activation section is three times less than the area of the perpendicular tangent plane of the adhesive section.

Furthermore, another scope of the invention is to provide a sperm selecting method for selecting a plurality of active sperms from an analyte comprising a plurality of sperms. The sperm selecting method comprises the steps of: preparing an analyte; preparing a flow channel module comprising an entrance, a working section and an exit, wherein the flow channel module comprises a fluid with a specified flow rate flowing from the entrance toward the exit; setting the plurality of sperms in the working section of the flow channel module corresponding to the entrance. Thus, the plurality of active sperms from the analyte can swim against the fluid with the specified flow rate and stay in place, and the plurality of sperms without activities will be flowed to the exit.

Furthermore, another scope of the invention is to provide a sperm selecting method for activating at least one sperm not revived to be selected again. The sperm selecting method comprises the steps of: preparing a flow channel module comprising a fluid with a specified flow rate; setting the sperm in the flow channel module; activating the sperm with a flow rate three times faster than the specified flow rate.

To sum up, one feature of the invention is that the analyte is set at the entrance of the flow field, instead of the exit of the system. Additionally, the activating design can be selectively added to the present invention for activating the sperms affected by the process of freeze storing. Accordingly, the invention reduces the attrition rate of the sperms in order to let the user obtain the selected sperms and solves the problem in the prior art.

DETAILED DESCRIPTION

To solve the problems in the prior art, the invention is to provide a sperm selecting system and method thereof. Compared to the prior art, the analyte is set at the entrance of the flow field, instead of the exit of the system. Thus, the invention reduces the attrition rate of the sperms. Additionally, the invention discloses a channel that the cross-sectional area of the channel enlarges gradually for reducing the flow rate of the fluid gradually. Thus, the sperms with different activities will be separated. Furthermore, the sperm selecting method can not only select a plurality of sperms from an analyte, but activate the sperms by increasing the flow rate.

The sperm selecting method is explained as follows. First, the sperm selecting method is used to select a plurality of active sperms from an analyte comprising a plurality of sperms. The sperm selecting method comprises the steps of preparing an analyte and a flow channel module. In the embodiment, the analyte can be, but not limited to pig sperms. The flow channel module comprises an entrance, a working section and an exit. Wherein, the flow channel module comprises a fluid with a specified flow rate flowing from the entrance toward the exit. Then, the sperms are set in the working section of the flow channel module corresponding to the entrance. The plurality of active sperms from the analyte can swim against the fluid with the specified flow rate and stay in place. The plurality of sperms without activities will be flowed to the exit. When necessary, the specified flow rate is defined as a flow rate of a fluid entering the entrance of the flow channel module. Additionally, compared to the prior art, the sperms is initially set in at the entrance instead of the end.

Furthermore, another scope of the invention is to provide a sperm selecting method for activating sperms not revived to be selected again. The sperm selecting method comprises the steps of: preparing a flow channel module comprising a fluid with a specified flow rate; setting the sperm in the flow channel module; activating the sperm with a flow rate three times to twenty times faster than the specified flow rate.

To be noticed, there is not a literature discloses or explains why the sperms will be activated by a fluid with a high flow rate. To be inferred, the high flow rate is like ejaculation so that the sperms will be activated. Additionally, the sperms is set at the entrance of the flow channel module, the attrition rate of the sperms will be reduced.

Figure 1:
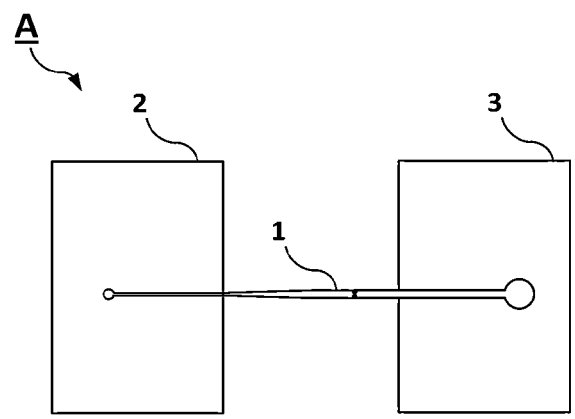
FIG. 1 illustrates a top view of a sperm selecting system according to an embodiment of the invention.
Figure 2:
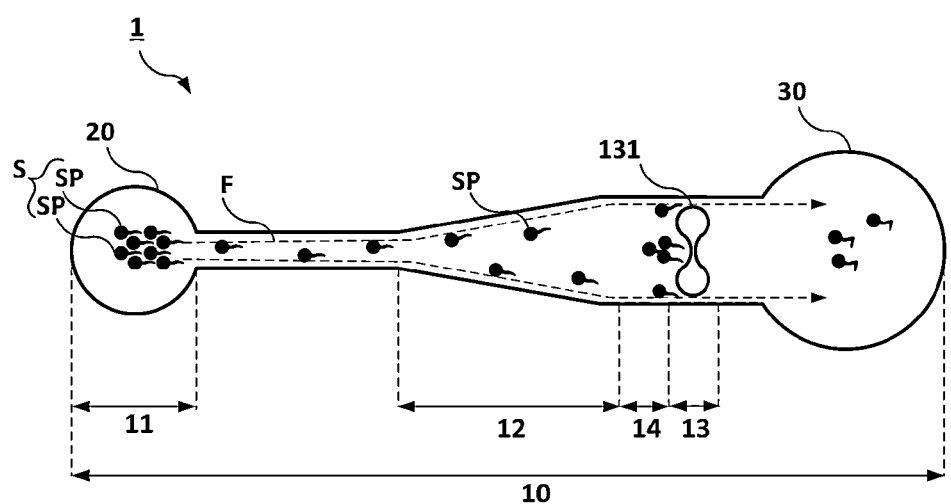
FIG. 2 illustrates a top view of a flow channel module of the sperm selecting system according to an embodiment of the invention.

The invention is to provide a sperm selecting system for selecting a plurality of active sperms from an analyte. Please refer to FIG. 1 and FIG. 2. FIG. 1 illustrates a top view of a sperm selecting system according to an embodiment of the invention. FIG. 2 illustrates a top view of a flow channel module of the sperm selecting system according to an embodiment of the invention.

In figures, the sperm selecting system A comprises a fluid supply module 2, a fluid collection module 3 and a flow channel module 1. Briefly, the fluid supply module 2 is used to provide a fluid F for the flow channel module 1. The fluid collection module 3 is used to receive the fluid F from the flow channel module 1. In the embodiment, the fluid supply module 2 is used to accommodate a liquid with a specified height for providing a continuous, steady flow field with a specified flow rate. Additionally, the fluid supply module 2 and the fluid collection module 3 are similar to the flow field system with hydraulic pressure difference in the prior art, so that the detail design will be omitted as follows.

Please refer to FIG. 2. In the embodiment, the flow channel module 1 comprises a working section 10, an entrance 20 and an exit 30. The entrance 20 is connected to the fluid supply module 2 to receive the fluid F with the specified flow rate. The exit 30 is connected to the fluid collection module 3 for receiving the fluid F. The working section 10 is disposed between and connected to the entrance 20 and the exit 30 for classifying and selecting the sperm SP. Additionally, the working section 10 comprises an initial section 11. The initial section 11 is disposed on the flow channel module 1 corresponding to the entrance 20, for selecting an analyte S which comprises a plurality of sperms SP.

In practice, the analyte S is set in the initial section 11. The fluid supply module 2 inputs the fluid F with the specified flow rate to the fluid collection module 3. At the same time, the plurality of active sperms SP can swim against the flow of the fluid F and stay in place. The plurality of sperms SP without activities will be flowed to the fluid collection module 3 by the fluid F.

Accordingly, the plurality of active sperms SP can stay in the initial section 11. Thus, the sperms SP can be avoided from damaging and the user can collect the sperms SP easily. Additionally, because the sperms SP stay in the initial section 11, the sperms SP have long time to revive and avoid from removing.

Figure 3A:
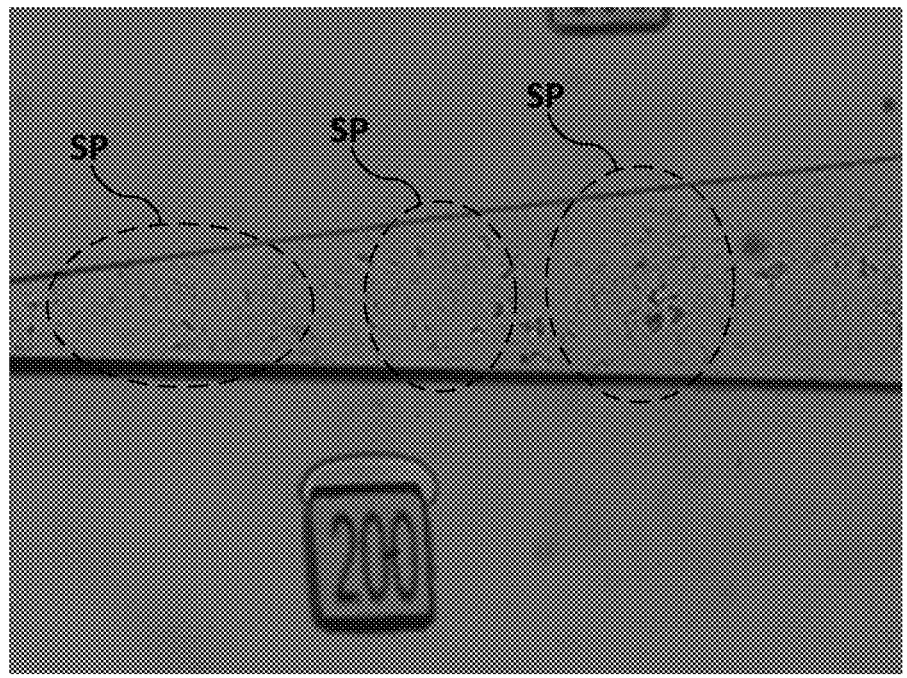
FIG. 3A and FIG. 3B illustrate a microphotograph with a real ratio in practice of a diverging section and an activation section according to an embodiment of the invention.

Furthermore, the working section 10 of the flow channel module 1 can selectively comprises a diverging section 12. Please refer to FIG. 2 and FIG. 3. FIG. 3A illustrates a microphotograph with a real ratio in practice of a diverging section and an activation section according to an embodiment of the invention. To be noticed, the ratio, size and relative position of each element can be a basis for modifying the description. In figures, the diverging section 12 is a channel which enlarges gradually. The flow rate of the fluid F is inversely proportional to the size of the channel. Thus, the diverging section 12 can be used to select the sperms with different activities in the corresponding section. Specifically, the flowing area of the perpendicular tangent plane for the fluid enlarges gradually from the entrance 20 toward the exit 30. In practice, a figure will be marked when the width of the diverging section 12 enlarges 100 μm. The flow rate of the fluid can be calculated by the formula of the fluid mechanics. To be noticed, the said area of the perpendicular tangent plane is a perpendicular tangent plane which is perpendicular to the groove's direction of the length of the flow channel module 1. Specifically, the area of the perpendicular tangent plane can be explained as the flowing area of the perpendicular tangent plane of the fluid. The area occupied by the material of the flow channel module 1 shall be omitted.

Figure 3B:
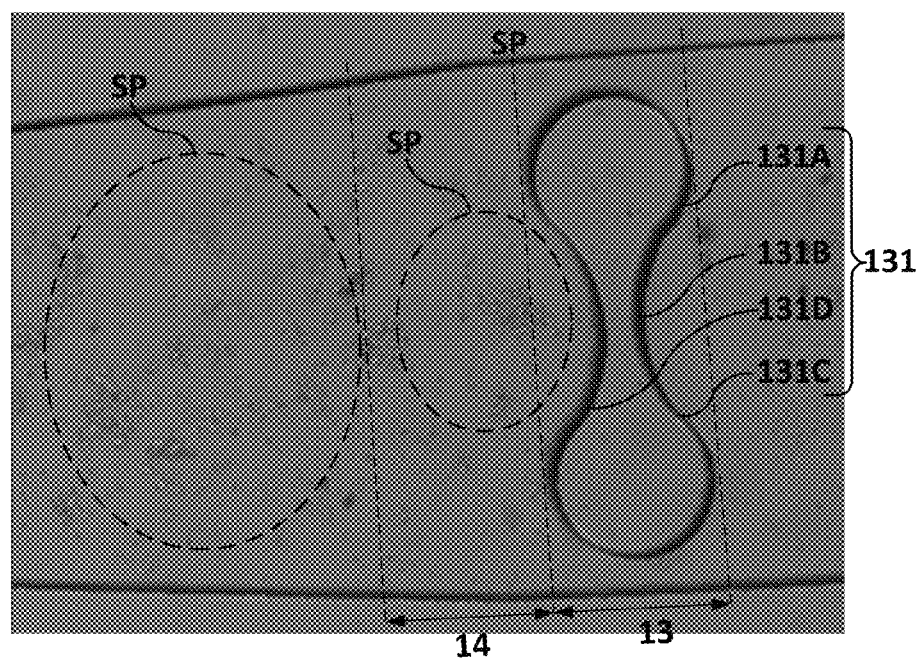

For activating the sperms SP which are not revived, the working section 10 can be selectively comprises an activation section 13. The flow rate of the fluid F in the activation section 13 can be, but not limited to at least three times faster than the specified flow rate. The flow rate of the fluid F in the activation section 13 can be three times to twenty times faster than the specified flow rate. Thus, the sperms SP which are not revived can be activated in the activation section 13. As shown in FIG. 2, the activation section 13 comprises an activation structure 131. The activation structure 131 is used to increase the flow rate of the fluid F through the activation section 13 by decreasing the flowing space. Specifically, please refer to FIG. 3B, FIG. 3B illustrates a microphotograph with a real ratio in practice of a diverging section and an activation section according to an embodiment of the invention. Thus, the ratio, size and relative position of each element can be a basis for modifying the description. In the embodiment, the activation structure 131 is a dumbbell shaped activation structure. The activation structure 131 comprises a head end 131A, a connecting end 131B and an extremity 131C. The connecting end 131B is disposed between the head end 131A and the extremity 131C. The head end 131A, the connecting end 131B and the extremity 131C are perpendicular to the flowing direction of the fluid F for letting the fluid F flow backward through the two ends of the activation structure 131.

Additionally, the head end 131A, the connecting end 131B and the extremity 131C are surrounded by a sperm-collecting groove 131D for storing the sperm SP. The sperm-collecting groove 131D comprises a depth. The groove's direction of the depth and the flowing direction of the fluid F are the same. Furthermore, the sperm-collecting groove 131D can separate the live sperms from the dead sperms. For specifically defining the activation section 13 and the activation structure 131, the working section 10 can comprises an adhesive section 14 which is adjacent and connected to the activation section 13. The adhesive section 14 can be located between the activation section 13 and the entrance 20 or the initial section 11. The average area of the perpendicular tangent plane of the flow channel module 1 in the activation section 13 is three times to twenty times less than the area of the perpendicular tangent plane of the adhesive section 14. The horizontal lengths of the flowing direction are the same in the adhesive section 14.

Figure 4:
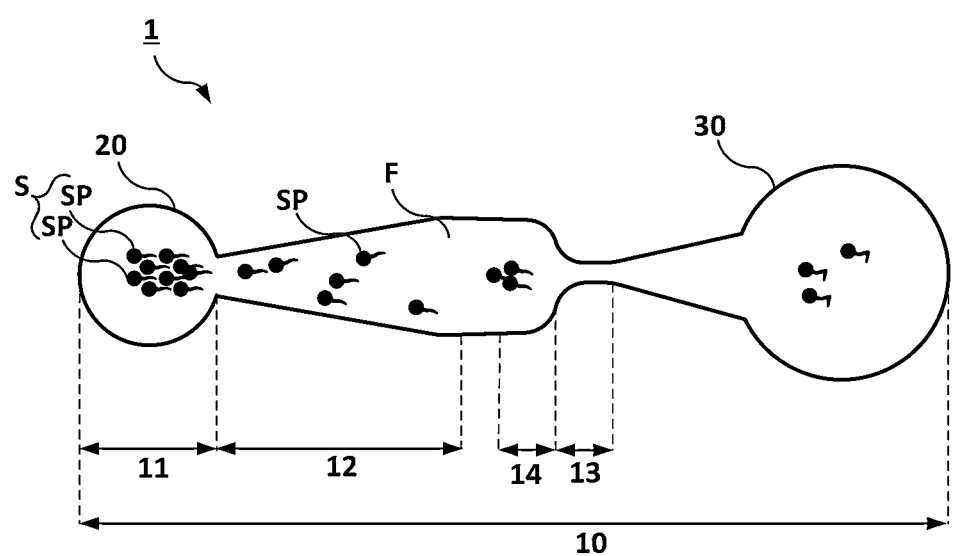
FIG. 4 illustrates a top view of a flow channel module of the sperm selecting system according to another embodiment of the invention.

To be noticed, the activation section 13 can be, but not limited to comprise an activation structure 131. As shown in FIG. 4, the shape of the flow channel module 1 can be changed in order to adjust the flow rate of the fluid F by changing the area of the perpendicular tangent plane.

To sum up, one feature of the invention is that the analyte is set at the entrance of the flow field, instead of the exit of the system. Additionally, the activating design can be selectively added to the present invention for activating the sperms affected by the process of freeze storing. Accordingly, the invention reduces the attrition rate of the sperms in order to let the user obtain the selected sperms and solves the problem in the prior art.

With the example and explanations above, the features and spirits of the invention will be hopefully well described.

Those skilled in the art will readily observe that numerous modifications and alterations of the device may be made while retaining the teaching of the invention. Accordingly, the above disclosure should be construed as limited only by the metes and bounds of the appended claims.

The invention claimed is:

1. A method of selecting a plurality of active sperm from a sample of sperm comprising:
   (A) providing a sperm selecting system, the system comprising,
      (I) a fluid supply module;
      (II) a fluid collection module;
      (III) a flow channel module, the flow channel comprising,
         (a) an entrance, the entrance connected to the fluid supply module;
         (c) an exit, the exit connected to the fluid collection module; and
         (c) a working section, the working section disposed between, the entrance and the exit, the working section comprising,
            (i) an initial section, the initial section disposed proximate to the entrance;
            (ii) an activation section, the activation section proximate to the exit, and wherein the activation section contains a dumbbell shaped activation structure, disposed in the activation section perpendicular to the longitudinal axis of the flow channel module; and
            (iii) a diverging section, the diverging section disposed between the initial section and the activation section, wherein the width of the flow channel module enlarges along the longitudinal axis of the flow channel module;
   (B) disposing the sample of sperm in the initial section;
   (C) supplying a fluid from the fluid supply module with a specified flow rate, such that the fluid flows from the fluid supply module through the flow channel module, to the fluid collection module, and wherein the positioning of the activation structure narrows the flow channel module such that fluid flows at least three times faster than the specified flow rate along the sides of the activation structure;
   (D) monitoring motility of sperm contained in the sperm sample, wherein motile sperm swim against the direction of flow and stay in the initial section, sperm with lower motility are flowed towards the fluid collection module but remain in the working section or the activation section, and sperm with no motility are flowed to the fluid collection module; and
   (E) selecting and collecting sperm contained in the initial section, the working section and/or the activation section.

2. The method of claim 1 further comprising a sperm collecting groove, the sperm collecting groove surrounding the dumbbell shaped activation structure.

3. The method of claim 1 further comprising an adhesive section, the adhesive section disposed between the initial section and the activation section.

4. A method of selecting and activating a sample of sperm previously tested and found to have low motility comprising:
   (A) providing a sperm selecting system, the system comprising;
      (I) a fluid supply module;
      (II) a fluid collection module;
      (III) a flow channel module, the flow channel module comprising;

(a) an entrance, the entrance connected to the fluid supply module;
(c) an exit, the exit connected to the fluid collection module; and
(c) a working section, the working section disposed between, the entrance and the exit, the working section comprising;
  (i) an initial section, the initial section disposed proximate to the entrance;
  (ii) an activation section, the activation section proximate to the exit, and wherein the activation section contains a dumbbell shaped activation structure, disposed in the activation section with the longitudinal axis of the dumbbell shaped activation structure perpendicular to the longitudinal axis of the flow channel module; and
  (iii) a diverging section, the diverging section disposed between the initial section and the activation section, wherein the width of the flow channel module enlarges along the longitudinal axis of the flow channel module;

(B) disposing the sample of previously tested sperm in the initial section;
(C) supplying a fluid from the fluid supply module at a specified flow rate, such that the fluid flows from the fluid supply module through the flow channel module to the fluid collection module, and wherein the positioning of the activation structure narrows the flow channel module such that fluid flows at least three times faster than the specified flow rate along the sides of the activation structure;
(D) monitoring motility of sperm contained in the sperm sample, wherein motile sperm swim against the direction of flow and stay in the initial section, sperm with lower motility are flowed towards the fluid collection module but remain in the working section or the activation section, and sperm with no motility are flowed to the fluid collection module; and
(E) selecting and collecting sperm contained in the initial section, the working section and/or the activation section.

\* \* \* \* \*